(12) United States Patent
Kapre et al.

(10) Patent No.: US 9,283,270 B2
(45) Date of Patent: Mar. 15, 2016

(54) METHOD FOR STABILIZATION OF BIOLOGICAL MOLECULES

(71) Applicant: Serum Institute of India Ltd., Pune (IN)

(72) Inventors: Subhash Vinayak Kapre, Maharashtra (IN); Sambhaji Shankar Pisal, Pune (IN); Nikhil Dattatray Avalaskar, Pune (IN)

(73) Assignee: Serum Institute of India Ltd., Pune (IN)

( * ) Notice: Subject to any disclaimer, the term of this patent is extended or adjusted under 35 U.S.C. 154(b) by 0 days.

(21) Appl. No.: 13/745,010

(22) Filed: Jan. 18, 2013

(65) Prior Publication Data

US 2013/0209503 A1   Aug. 15, 2013

(51) Int. Cl.

| A61K 39/00 | (2006.01) |
|---|---|
| A61K 39/385 | (2006.01) |
| A61K 45/00 | (2006.01) |
| A61K 47/00 | (2006.01) |
| A61K 39/38 | (2006.01) |
| A61K 39/095 | (2006.01) |
| A61K 38/00 | (2006.01) |

(52) U.S. Cl.
CPC ............ *A61K 39/385* (2013.01); *A61K 39/095* (2013.01); *A61K 38/00* (2013.01); *A61K 39/0011* (2013.01); *A61K 2039/6037* (2013.01); *C07K 2319/00* (2013.01)

(58) Field of Classification Search
None
See application file for complete search history.

(56) References Cited

U.S. PATENT DOCUMENTS

| 5,618,539 A | 4/1997 | Dorval et al. |
|---|---|---|
| 5,728,386 A | 3/1998 | Provost et al. |
| 2010/0203137 A1* | 8/2010 | Contorni et al. ............... 424/484 |
| 2010/0285069 A1* | 11/2010 | Contorni et al. ............ 424/250.1 |
| 2013/0071422 A1* | 3/2013 | Pallaoro et al. ............ 424/189.1 |

FOREIGN PATENT DOCUMENTS

| EP | 1123710 B1 | 3/2005 |
|---|---|---|
| WO | 9828000 | 7/1998 |
| WO | 0141800 A2 | 6/2001 |
| WO | 2009111849 A1 | 9/2009 |

OTHER PUBLICATIONS

Who Expert Committee on Biological Standardization, World Health Organization, Geneva 2000.
Immunogenicity of *Streptococcus pneumoniae* type 6B and 14 polysaccharide-tetanus toxoid conjugates and the effect of uncoupled polysaccharide on the antigen-specific immune response, Vaccine 1998, vol. 16, No. 20, pp. 1941-1949.

* cited by examiner

*Primary Examiner* — Gary Nickol
*Assistant Examiner* — Lakia Tongue
(74) *Attorney, Agent, or Firm* — Kinney & Lange, P.A.

(57) ABSTRACT

Thermostable polysaccharide based lyophilized vaccines are disclosed, particularly polysaccharide-protein conjugate vaccines and methods for preparation thereof. In an exemplary embodiment, a stabilized vaccine composition consists essentially of at least one polysaccharide-protein conjugate, at least one amorphous excipient, and a buffer component.

6 Claims, 1 Drawing Sheet

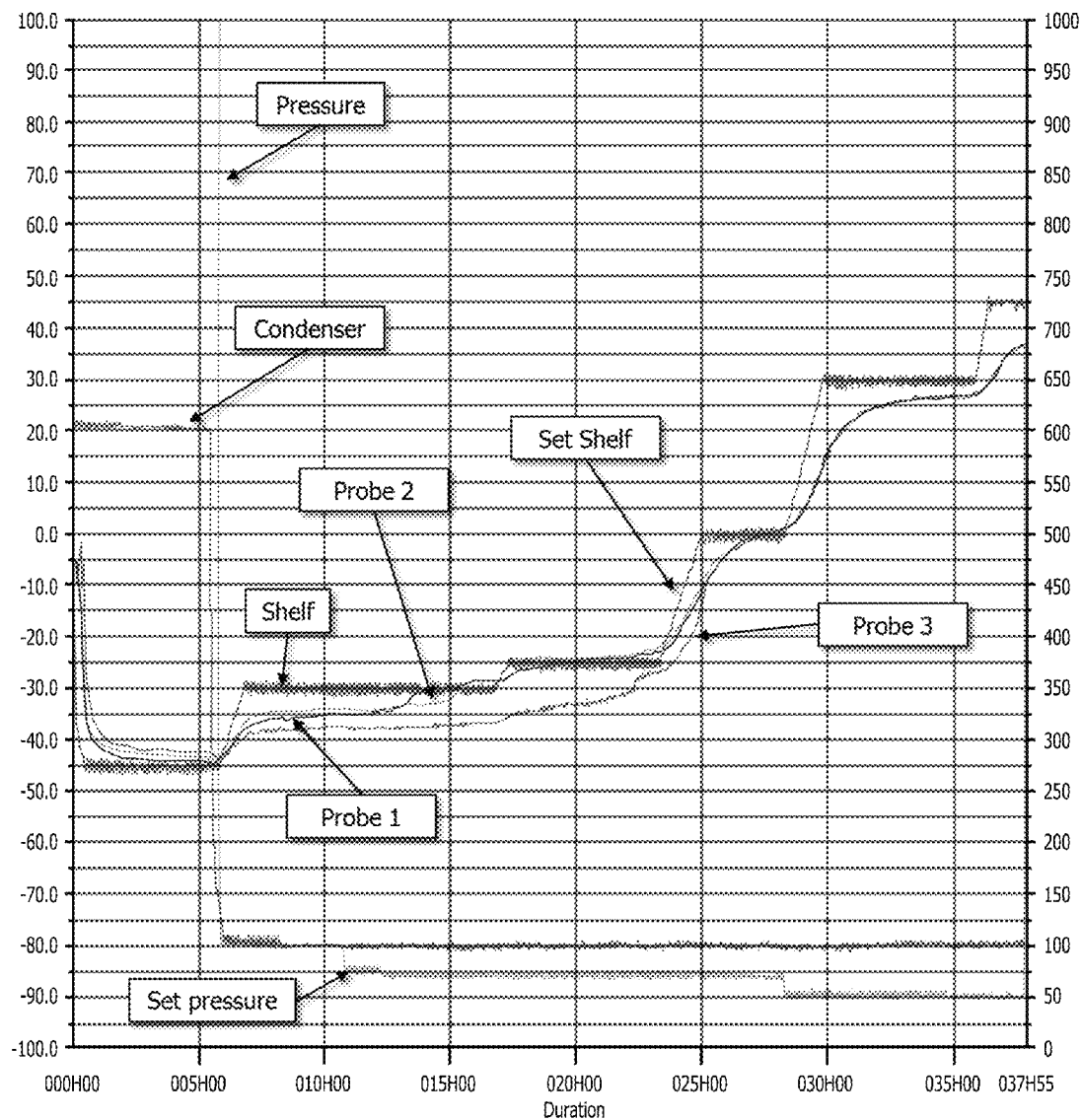

METHOD FOR STABILIZATION OF BIOLOGICAL MOLECULES

CROSS-REFERENCE TO RELATED APPLICATION(S)

This application claims priority under 35 U.S.C. 119 to Indian Patent Application No. 206/MUM/2012 filed Jan. 20, 2012, the disclosure of which is hereby incorporated by reference.

BACKGROUND

Vaccines are widely used for the prevention and/or therapy of many different diseases. Vaccine utilizing polysaccharide (PS) alone has relatively low immunogenicity. To overcome the relatively low immunogenicity of polysaccharide, PS vaccines are conjugated to protein carriers to increase immunogenicity and provide long-term protection in young children. Many conjugate vaccines are already approved and marketed throughout the world. Examples of such vaccines, known as "conjugates" are available for *Haemophilus influenzae* type b (e.g., ACTHIB® [Haemephilus b conjugate vaccine, Tetanus toxoid conjugate], HIBERIX [Hamemophilus b conjugate vaccine, Tetanus toxoid conjugate]), *Neisseria meningitides* types A, C, W and Y (e.g., MENACTRA® [Meningococcal (Groups A, C, y and W135) Polysaccharide Diphtheria Toxoid Tetanus conjugate vaccine]) and *S. pneumoniae* (e.g., PREVNAR® [Pneumococcal 7-valent conjugate vaccine (Diphtheria CRM197 Protein], SYNFLORIX® [Pneumococcal conjugate vaccine (Non-Typeable *Haemophilus influenza* (NTHi) protein D, Diptheria or tetanus toxoid conjugates]).

To extend the shelf-life of conjugate vaccines, formulations are often lyophilized. Lyophilization of conjugate, however, can lead to protein aggregation during freezing and storage. As aggregation increases, the effective concentration of available immunogen decreases this may result loss of immunogenicity. Also the lyophilization processes involving freezing and sublimation have stresses which result into chemical degradation which subsequently releases free polysaccharide.

Disaccharides are used as stabilizers during the process of lyophilization. The role of a disaccharide is to provide water replacement and subsequent hydrogen bond formation with polysaccharide protein conjugate. Also disaccharides form sugar glasses of extremely high viscosity. The conjugate and water molecules are immobilized in the viscous glass, leading to extremely high activation energies required for any reactions to occur. The role of crystalline glass former with sugar is to form glassy matrix with the conjugate or mixture of conjugates arresting any degradation.

The polysaccharide component of conjugate vaccines undergoes gradual depolymerization at a rate that depends on the type of conjugate, formulation components and storage conditions. This causes reduction in molecular size of the polysaccharide component, i.e. an increase in free polysaccharide. Hence tests should be conducted to ensure stability of product.

The immunogenicity of a Polysaccharide-protein conjugate vaccine is decreased by the presence of uncoupled Polysaccharide, wherein the magnitude of this effect seems to be Polysaccharide type dependent. Refer Rodriguez et al (1998), "Immunogenicity of *Streptococcus pneumoniae* type 6B and 14 polysaccharide-tetanus toxoid conjugates and the effect of uncoupled polysaccharide on the antigen-specific immune response," Vaccine, 16(20), 1941-1949.

Polysaccharide-carrier protein conjugates are known to release free polysaccharide after conjugation while further processing, lyophilization or storage in liquid as well as solid formulations. Clinical protection is conferred only by polysaccharide that is covalently bound to the carrier protein. Accordingly vaccines demonstrating adequate immunogenicity and thermostability contain amounts of unbound polysaccharide ranging from less than 10% of the total polysaccharide, refer WHO TRS, pg 47-48, No. 897, 2000.

Also the average residual moisture content of less than 2.5% is desired, refer WHO TRS, pg 45, No. 897, 2000. Further accelerated and real-time studies are additional parameters that provide supporting evidence for stability.

U.S. Pat. No. 5,618,539 describes stabilized viral vaccines, particularly against polio, comprising an aqueous solution of live virus and a stabilizing compound, which has at least two amino or imino groups, such as basic amino acids (e.g. lysine, arginine etc.). This patent mentions also that the stabilizing compound allows a thermal stability increase of the virus in relation to stabilized viruses by magnesium chloride ($MgCl_2$) (another stabilizing agent). But even with the use of effective stabilizers, as magnesium chloride or amino acids, nothing stops the vaccine potency loss, if it is thawed during the transport or storage. Rombaut et al. (B. Rombaut, B. Verheyden, K. Andries and A. Boeye).

WO 2009/111849 A1 discloses a method for producing a stabilized polio virus vaccine composition in liquid form by applying high hydrostatic pressure.

U.S. Pat. No. 5,728,386 discloses a process for making thermostable varicella zoster virus vaccine, wherein the lyophilized or liquid preparation of live attenuated VZV was heated under highly inactivating conditions.

WO/1998/028000 discloses thermostable vaccine formulations comprising an increased amount of a 6-carbon polyhydric alcohol (such as sorbitol), an increased amount of a disaccharide (such as sucrose) and an amount of a physiologically active buffer to adjust the pH from about 6.0 to about 7.0.

EP1123710 discloses a thermostable Hepatitis A vaccine formulation which can be stored at ambient temperature for a longer time.

WO/2001/041800 discloses a method for stabilizing a MenC vaccine upon lyophilization comprising: (a) dissolving the MenC vaccine in a dissolution buffer comprising at least one amorphous excipient (sucrose) and an amorphous buffer (histidine) to form a mixture, and (b) lyophilizing the mixture.

Despite these advances in the area of vaccine formulations, there remains a distinct need for conjugate vaccine formulations with improved thermostability, shelf-life and immunogenicity especially meningococcal and pneumococcal conjugate vaccines. None of the prior art stabilizers impart the desired enhanced sustained level of stability. The present invention addresses and meets the long felt need for a stabilizer and conjugate vaccine formulation with increased thermostability subsequent to lyophilization.

The present invention arises from the surprising discovery that it is possible to prepare lyophilized polysaccharide protein conjugate vaccines by utilizing a specific stabilizer combination of amorphous excipients and buffer resulting in improved thermostability and immunogenicity.

SUMMARY

The instant invention relates to lyophilized polysaccharide-protein conjugate vaccine compositions consisting essentially of: i) at least one polysaccharide-protein conjugate, ii) at least one amorphous excipient and iii) a buffer; thereby providing a stabilized conjugate vaccine that exhibits a free polysaccharide content of less than 11% w/w over a 6 month period when stored at 40° C.

Accordingly in a first embodiment, said thermostable polysaccharide protein conjugate vaccine has following advantageous features a) accelerated stability studies at 40° C. indicating a free-polysaccharide level of less than 11%; b) residual moisture of less than 2%; c) uniform lyophilized product; d) release/movable pellet type of cake structure with high solubility with reconstitution time less than 30 seconds and aesthetically pleasant appeal and e) lyophilization cycle duration of about 40 hrs.

In a second embodiment, the lyophilized formulation of the instant invention comprises i) at least one polysaccharide-protein conjugate, ii) at least one amorphous excipient in the range of 1% to 10% w/v, iii) at least one buffer in the range of 0.05% to 2% w/v and iv) has pH from 6 to about 7.

Although the invention is not limited to the use of any specific excipients, particularly suitable excipients include amorphous excipients selected from the group consisting of monosaccharides, disaccharides, oligosaccharides and polysaccharides. More specifically said amorphous excipient can be selected from the group consisting of dextrose, sucrose, lactose, trehalose, xylose, cellobiose, raffinose, isomaltose and cyclodextrins.

Optionally the stabilizer mixture of present invention can further contain suitable crystalline carbohydrates, sugars and sugar alcohols like mannitol, sorbitol and allitol.

The buffering agent of the instant invention can be selected from but not limited to mono sodium citrate, di sodium citrate, tri sodium citrate with or without their hydrated form or anhydrous form or any combination thereof.

In an aspect of the second embodiment, the lyophilized formulation of the instant invention comprises i) at least one polysaccharide-protein conjugate, ii) two disaccharides in the range of 2 to 4% w/v each, iii) a buffer in the range of 0.25% to 0.75% w/v and iv) has pH from 6 to about 6.5.

In another aspect of the second embodiment, said stabilized immunogenic composition can comprise stabilizer combinations selected from a group consisting of:
a) 2% (w/v) Trehalose and 0.5% sodium citrate;
b) 3% (w/v) Trehalose and 0.5% sodium citrate;
c) 3% (w/v) Sucrose and 0.5% sodium citrate;
d) 3% (w/v) Sucrose, 2 to 2% (w/v) Lactose and 0.5% sodium citrate; and
e) 3% (w/v) Trehalose, 2% (w/v) Lactose and 0.5% sodium citrate.

In a third embodiment, said lyophilized polysaccharide protein conjugate formulation can have at least 6 month stability at 40° C., wherein the free polysaccharide content can be less than 11% w/w.

In an aspect of the fourth embodiment, a method for lyophilization of a mixture containing at least one polysaccharide protein conjugate, at least one amorphous excipient and a buffer comprises of following steps:
i) Freezing up to −45° C. with freezing rate of 5 to 10° C./minute;
ii) Final freezing temperature of −45° C.;
iii) Frozen mass held between −40 to −50° C. for 5 hrs;
iv) Primary drying achieved by increasing the temperature from −45 to −30° C. in 1 hr, holding for 10 hrs, at pressure of 100 μbar; primary drying further achieved by increasing the temperature from −27 to −23° C. in 30 min, holding for 6 hrs, at pressure of 70 μbar; primary drying further achieved by increasing the temperature from −5 to 5° C. in 100 min, holding for 3.5 hrs, at pressure of 70 μbar;
v) Heating ramp for secondary drying involving change in temperature from −5 to 35° C., achieved in 1.5 hrs, at pressure of 50 μbar;
vi) Secondary drying achieved at a temperature between 20 to 30° C., for 5 to 7 hrs, at pressure of 50 μbar;
vii) Secondary drying further achieved at a temperature between 40 to 50° C., for 1 to 2 hrs, at pressure 30 to 70 μbar, preferably at 50 μbar; and
viii) Backfilling of vials with nitrogen at pressure of 700 μbar.

In a fifth embodiment, said polysaccharide-protein conjugate comprises polysaccharides or oligosaccharides selected from but not limited to meningococcal polysaccharides of serogroups A, B, C, D, X, Y, Z, 29E and W-135.

A further aspect of the instant invention is that said polysaccharide-protein conjugate vaccine composition of instant invention can contain a monovalent polysaccharide protein conjugate alone or a multivalent mixture thereof. Optionally said composition can contain at least one bivalent polysaccharide-protein conjugate.

BRIEF DESCRIPTION OF THE DRAWINGS

FIG. 1 depicts a Lyophilization chart indicating implementation of a recipe according to an embodiment of the present invention.

DETAILED DESCRIPTION

Definitions

As used herein, the term "biological molecule" includes, but is not limited to, proteins, nucleic acids, and saccharides. In a preferred embodiment of the present invention, the biological molecule is a polysaccharide based immunogen. In a more preferred embodiment, the biological molecule is a plain polysaccharide or polysaccharide-carrier protein conjugate. As used herein, the term "protein" refers to polypeptides, peptides, and analogs thereof. "Protein" also includes polypeptides and peptides which are conjugated to other biological molecules. In a preferred embodiment of the present invention, the protein is an immunogen.

As used herein, the term "polysaccharide" includes capsular polyoses and oligosaccharides selected from but not limited to meningococcal polysaccharides of serogroups A, B, C D, X, Y, Z, 29E, W-135; pneumococcal polysaccharides of serogroups 1, 2, 3, 4, 5, 6A, 6B, 7F, 8, 9N, 9V, 10A, 11A, 12F, 14, 15B, 17F, 18C, 19F, 19A, 20, 22F, 23F, and 33F; meningococcal polysaccharides of serotypes, *Haemophilus influenzae* type b polysaccharide polyribosylribitol phosphate, group B streptococcal polysaccharides of serotypes III and V and *Salmonella typhi* Vi polysaccharide. Other polysaccharides of pneumococcal and group B streptococcal serotypes are also suitable for use herein, as are other T-independent polysaccharide and oligosaccharide antigens, for example, polysaccharides or oligosaccharides derived from group A *streptococcus, Staphylococci, Enterococci, Klebsiella pneumoniae, E. coli, Pseudomonas aeruginosa,* and *Bacillus anthracis*. While bacterial polysaccharides and oligosaccharides are particularly preferred, gram (−) bacterial lipopolysaccharides and lipooligosaccharides and their polysaccharide and oligosaccharide derivatives, and viral polysaccharides and oligosaccharides can also be employed.

As used herein, the term "carrier protein" includes proteins from the group of CRM 197, diphtheria toxoid, tetanus toxoid, pertussis toxoid, E. coli LT, E: coli ST, and exotoxin A from *Pseudomonas aeruginosa*, outer membrane complex c (OMPC), porins, transferrin binding proteins, pneumolysin, pneumococcal surface protein A (PspA), pneumococcal adhesin protein (PsaA), pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD).

A "bivalent conjugate" is a polysaccharide protein conjugate wherein two different types of capsular polysaccharides are conjugated to the same carrier protein molecule of the protein carrier.

Lyophilization may be performed in a container, such as a tube, a bag, a bottle, a tray, a vial (e.g., a glass vial), syringe or any other suitable containers. The containers may be disposable. Inventive methods in accordance with the present invention can be carried out using various lyophilizers, such as, commercial-scale lyophilizers, pilot-scale lyophilizers, or laboratory-scale lyophilizers.

The lyophilized vaccine composition of the present invention can be reconstituted with a delivery vehicle having pH from about 6 to 7.5, particularly with saline or PBS.

The lyophilized vaccine composition of the instant invention can be given as a 1, 5 or 10 dose formulation.

Although the foregoing invention is described herein in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

Example 1

Bulk Formulation Preparation\

The quantity of sugars and citrate salt were weighed and dissolved in water for injection as per below mentioned concentrations. Bulk Meningococcal A Tetanus Toxoid conjugate was added to 240 mcg/ml and pH was adjusted to 6.5±0.5 by addition of 1N HCl or 1NaOH.

TABLE 1

| Sr. No. | Stabilizers | Amount in Liquid Formulation | Amount per vial |
|---|---|---|---|
| 1 | Sucrose and Lactose | 3% and 2% w/v respectively | 15 mg and 10 mg |
| 2 | Trehalose and Lactose | 3% and 2% w/v respectively | 15 mg and 10 mg |
| 3 | Sucrose and Sodium citrate | 3% and 0.5% w/v respectively | 15 mg and 2.5 mg |
| 4 | Trehalose and Sodium citrate | 3% and 0.5% w/v respectively | 15 mg and 2.5 mg |
| 5 | Trehalose and Sodium citrate | 2% and 0.5% w/v respectively | 10 mg and 2.5 mg |
| 6 | Sucrose, Lactose and Sodium citrate | 3%, 2% and 0.5% w/v respectively | 15 mg, 10 mg and 2.5 mg |
| 7 | Trehalose, Lactose and Sodium citrate | 3%, 2% and 0.5% w/v respectively | 15 mg, 10 mg and 2.5 mg |

Sucrose: AR Grade; Lactose: Lactose Monohydrate; Sodium Citrate: Trisodium Dihydrate Further final volume was made up with WFI. Bulk formulations of Men C-CRM197 were prepared in a similar manner.

Example 2

Lyophilization Recipe

The formulated bulk (Men A-TT & Men C-CRM197) were filled into the vials as 0.5 ml/vial. The filled vials were subjected to the below given lyophilization cycle. Nitrogen back-filling was done at 700 µbar pressure.

TABLE 2

| Precooling | | | |
|---|---|---|---|
| Shelf Precooling | Yes | 8° C. | — |

| Freezing | | | |
|---|---|---|---|
| Shelf Temp Control | Final T ° C. | Ramp Duration (Min) | Soak Duration (Min) |
| Ramp 1 & soak 1 | −45 | 1 | 360 |

| Sublimation | | | |
|---|---|---|---|
| Shelf Temp Control | Final T ° C. | Ramp Duration (Min) | Soak Duration (Min) |
| Ramp 1 & Soak 1 | −30 | 60 | 600 |
| Ramp 2 & Soak 2 | −25 | 30 | 360 |
| Ramp 3 & Soak 3 | 0 | 100 | 200 |
| Ramp 4 & Soak 4 | 30 | 90 | 360 |

Chamber pressure control
100 µbar for first 300 min, 70 µbar for next 1050 min, 50 µbar for 450 min.

| Secondary Drying | | | |
|---|---|---|---|
| Shelf Temp Control | Final T ° C. | Ramp Duration (Min) | Soak Duration (Min) |
| Ramp 1 and soak 1 | 45 | 30 | 90 |

Chamber pressure control
50 µbar for 120 min.

Example 3

Stability Studies

Post-lyophilization, the vials were incubated at 40° C. up to 6 months. Sampling points were kept at 1 month, 2 months, 3 months and 6 months.

Following were the steps utilized for analysis of unbound (free) polysaccharide for Men A-TT conjugate: i) cakes were reconstituted with water for injection and analyzed immediately for free polysaccharide estimation, ii) reconstituted product was subjected to DOC precipitation, iii) precipitate of conjugate was separated by centrifugation and supernatant was analyzed for presence of polysaccharide by Phosphorous assay, iv) % free polysaccharide was calculated on weight basis.

TABLE 3

Meningococcal A-TT Conjugate vaccine
Unbound (free) polysaccharide (%) at 40° C.

| Formulation | Initial | 1 month | 2 month | 3 month | 6 month |
|---|---|---|---|---|---|
| 3% Sucrose and 2% Lactose | 8.12 | 10.07 | 10.19 | 10.61 | 10.88 |
| 3% Trehalose and 2% Lactose | 8.58 | 8.89 | 9.05 | 9.85 | 10.78 |
| 3% Sucrose and 0.5% Sodium citrate | 4.92 | 5.00 | 5.60 | 7.13 | 9.56 |
| 3% Trehalose and 0.5% Sodium citrate | 4.84 | 6.01 | 6.86 | 6.88 | 8.99 |
| 2% Trehalose and 0.5% Sodium citrate | 5.60 | 6.66 | 7.29 | 7.89 | 9.02 |
| 3% Sucrose, 2% Lactose and 0.5% Sodium citrate | 7.52 | 6.25 | 7.81 | 8.15 | 8.45 |
| 3% Trehalose, 2% Lactose and 0.5% Sodium citrate | 6.62 | 6.65 | 8.08 | 9.56 | 10.30 |

Above data indicates that sodium citrate in various combinations with trehalose, sucrose and lactose results in free polysaccharide content of less than 11% w/w over a 6 month period.

For Men C-CRM197 conjugate analysis of unbound (free) polysaccharide was done by resorcinol assay followed by % free polysaccharide calculation (weight basis).

TABLE 4

Meningococcal C-CRM197 Conjugate vaccine
Unbound (free) polysaccharide (%) at 40° C.

| Formulation | Initial | 1 month | 2 month | 3 month | 6 month |
|---|---|---|---|---|---|
| 3% Sucrose and 2% Lactose | 2.13 | 2.58 | 3.59 | 5.04 | 3.00 |
| 3% Trehalose and 2% Lactose | 1.96 | 2.16 | 2.57 | 4.33 | 2.27 |
| 3% Sucrose and 0.5% Sodium citrate | <0.96 | <0.98 | <1.06 | <1.09 | 2.74 |
| 3% Trehalose and 0.5% Sodium citrate | 1.31 | 2.10 | 2.20 | 3.01 | 3.21 |
| 2% Trehalose and 0.5% Sodium citrate | 1.64 | 2.19 | 2.74 | 3.46 | 2.05 |
| 3% Sucrose, 2% Lactose and 0.5% Sodium citrate | 1.54 | 2.37 | 2.50 | 3.31 | 2.74 |
| 3% Trehalose, 2% Lactose and 0.5% Sodium citrate | 1.48 | 2.75 | 3.23 | 3.79 | 2.09 |

Above data indicates that sodium citrate in various combinations with trehalose, sucrose and lactose results in free polysaccharide content of less than 3% w/w over a 6 month period.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A stabilized vaccine composition, consisting essentially of: i) at least one polysaccharide-protein conjugate; ii) sucrose at a concentration of approximately 3% w/v; and iii) sodium citrate at a concentration of approximately 0.5% w/v, wherein the composition contains less than 11% free polysaccharide by weight over a six month period when stored at 40° C.

2. A composition according to claim 1, wherein the said conjugate comprises a capsular polysaccharide of *Neisseria meningitides* (*N. meningitidis*) selected from a serogroup A, B, C, D, X, Y, Z, 29E and W-135.

3. A composition according to claim 2, wherein the said *N. meningitidis* capsular polysaccharide is selected from a serogroup A, C, X, Y, and W-135.

4. A composition according to claim 1, wherein the polysaccharide-protein conjugate comprises CRM197 or tetanus toxoid.

5. A method for lyophilization of a mixture containing at least one polysaccharide protein conjugate, sucrose at a concentration of approximately 3% w/v and sodium citrate at a concentration of approximately 0.5% w/v, the method comprising i) Freezing up to −45° C. with freezing rate of 5 to 10° C./minute; ii) Final freezing temperature between −40 to 50° C.; iii) Frozen mass held between −40 to −50° C. for up to 6 hrs; iv) Primary drying achieved by increasing the temperature from −45 to −30° C. in 30 min to 2 hr., holding for 8 to 12 hrs, at pressure 75 to 125 μbar; primary drying further achieved by increasing the temperature from −27 to −23° C. in 15 min to 1 hr., holding for 4 to 8 hrs, at pressure 50 to 100 μbar; primary drying further achieved by increasing the temperature from −5 to 5° C. in 50 min to 1.5 hr., holding for 3 to 4 hrs, at pressure 50 to 100 μbar; v) Heating ramp for secondary drying involving change in temperature from −5 to 35° C., achieved in 1 to 2 hrs, at pressure 30 to 70 μbar; vi) Secondary drying achieved at a temperature above 25° C., for 5 to 7 hrs, at pressure 30 to 70 μbar; vii)) Secondary drying further achieved at a temperature above 40° C., for 1 to 2 hrs, at pressure 30 to 70 μbar; and viii) Backfilling of vials with inert gases at pressure 500 to 100 μbar, wherein said mixture contains less than 11% free polysaccharide by weight over a six month period when stored at 40° C.

6. A method for lyophilization of a mixture containing at least one polysaccharide protein conjugate, sucrose at a concentration of approximately 3% w/v and sodium citrate at a concentration of approximately 0.5% w/v, the method comprising: i) Freezing up to −45° C. with freezing rate of 5 to 10° C./minute; ii) Final freezing temperature of −45° C.; iii) Frozen mass held between −40 to −50° C. for 5 hrs; iv) Primary drying achieved by increasing the temperature from −45 to −30° C. in 1 hr., holding for 10 hrs, at pressure of 100 μbar; primary drying further achieved by increasing the temperature from −27 to −23° C. in 30 min, holding for 6 hrs, at pressure of 70 μbar; primary drying further achieved by increasing the temperature from −5 to 5° C. in 100 min, holding for 3.5 hrs, at pressure of 70 μbar; v) Heating ramp for secondary drying involving change in temperature from −5 to 35° C., achieved in 1.5 hrs, at pressure of 50 μbar; vi) Secondary drying achieved at a temperature between 20 to 30°

C., for 5 to 7 hrs, at pressure of 50 μbar; vii) Secondary drying further achieved at a temperature between 40 to 50° C., for 1 to 2 hrs, at pressure 30 to 70 μbar, preferably a 50 μbar; and viii) Backfilling of vials with nitrogen at pressure of 700 μbar, wherein said mixture contains less than 11% free polysaccharide by weight over a six month period when stored at 40° C.

* * * * *